United States Patent [19]

Ganesh et al.

[11] Patent Number: 5,165,921
[45] Date of Patent: Nov. 24, 1992

[54] METHOD FOR TREATING CONDYLOMA ACUMINATUM WITH INTERFERON

[75] Inventors: Orekonde Ganesh, Bloomfield Hills, Mich.; William E. Stewart, Lutz, Fla.

[73] Assignee: National Geno Sciences, Inc., Southfield, Mich.

[21] Appl. No.: 673,850

[22] Filed: Mar. 21, 1991

Related U.S. Application Data

[63] Continuation of Ser. No. 299,707, Jan. 23, 1989, abandoned.

[51] Int. Cl.$^5$ .............................................. A61K 45/02
[52] U.S. Cl. .................................. 424/85.7; 424/85.4; 530/351
[58] Field of Search ........................... 424/85.7, 85.4; 530/351

[56] References Cited

U.S. PATENT DOCUMENTS

| | | | |
|---|---|---|---|
| 3,981,991 | 9/1976 | Stewart et al. | 424/85.4 |
| 3,981,991 | 9/1976 | Stewart et al. | |
| 4,017,600 | 4/1977 | Stewart et al. | |
| 4,389,395 | 6/1983 | Lerner et al. | |
| 4,462,985 | 7/1984 | Cummins, Jr. | |
| 4,462,986 | 7/1984 | Smith | |
| 4,496,537 | 1/1985 | Kwan | |
| 4,604,284 | 8/1986 | Kung et al. | |
| 4,675,184 | 6/1987 | Hasegawa et al. | 424/85.4 |
| 4,959,210 | 9/1990 | Smiles et al. | 424/85.7 |

FOREIGN PATENT DOCUMENTS 0077063 6/1982 European Pat. Off.

OTHER PUBLICATIONS

Ikic et al., Proc Symposium on Chemical Use of Interferon, Yugoslav Academy of Sciences and Arts, Oct. 1975, pp. 235-238.
Smiles et al., The Biology of the Interferon System, 1869, Cantell et al., ed, pp. 493-501.
Friedman-Kien et al., JAMA, vol. 259, No. 4, pp. 533-538, 1988.
Gall et al., Obstetrics and Gynecology, vol. 67, No. 5, 1986, pp. 643-651.
Evon et al, New Engl. J. Med., vol. 315, No. 17, 1986, pp. 1059-1064.
Ikic, D. et al. (1975). "Preliminary Study of the Effect of Human Leukocytic Interferon on Condylomata Acuminata in Women." Proc. Symp. Clinical Use of Interferon, Yugoslav, Acad. Sci. & Arts, Zagreb, Yugoslavia, pp. 223-227.
Ikic, D. et al. (1975). "Double Blind Clinical Study With Human Leukocyte Interferon in the Therapy of Condylomata Acuminata." Proc. Symp. Clinical Use of Interferon, Yugoslav. Acad. Sci. & Arts, Zagreb, Yugoslavia, pp. 229-233.
Friedman-Kien, A. E., et al. (1988). "Natural Interferon Alfa for Treatment of Condylomata Acuminata." JAMA 253, 533-38.
Eron L. J. et al. (1986). "Interferon Therapy for Condylomata Acuminata." N. Engl. J. Med. 315, 1059-64.
Gall, S. A. et al. (1986). "Efficacy of Human Lymphoblastoid Interferon in the Therapy of Resistant Condyloma Acuminata." Obstet. Gyncol. 67, 643-51.
Ikic, D. et al. (1975) "Therapeutical Effect of Human Leukocyte Interferon Incorporated into Ointment and Cream on Condylomata Acuminata." Proc. Symposium on Clinical Use of Interferon, Yugoslav Acad. Sci. & Arts 234-38.
Smiles, K. et al. (1986). "Activity of Intralesional Interferon Alpha-2B in Viral and Malignat Skin Diseases" in The Biology of the Interferon System (Cantell et al., eds) 493-501.
(Internal Report, National Geno Sciences) Ramesh, T. "Expert Report on the Clinical Documentation".
(Internal Report, National Geno Scienses) Roberts, W. S. "A Double Blind, Placebo-Controlled, Crossover Trial of Human Interferon-Alpha."
(Internal Report, National Geno Scienses) "Part IV: Clinical Documentation."
(Vesterine, E. et al. (1984). "Treatment of Vaginal Flat Condyloma With Interferon Cream." Lancet 157.
Marcovici, R. et al. (1983). "Human Fibroblast Interferon Therapy in Patients With Condyloma Acuminata." Israel J. Med. Sci. 19, 104.
Vesterinen, E. et al. (1984). "Topical Treatment of Flat Vaginal Condyloma With Human Leukocyte Interferon." Obstet. Gynecol. 64, 535-538.
Keay, S. et al. (1988). "Topical Interferon For Treating Condyloma Acuminata in Women." J. Infect. Dis. 158, 934-39.
Brzoska, J. et al. "Phase II Clinical Trials of Interferon, Beta Gel (Fiblaferongel) in Determatological Diseases." Abstract B4-7, p. 259) Source not apparent) (abstract only).
Schonfeld, A. et al. (1984). "Intramuscular Human Interferon-Beta Injections in Treatment of Condylomata Acuminata." Lancet 1038-42.
Douglas, J. M., Jr., et al. (1986). "Effect of Asymptomatic Infection with HTLV-III on the Response of Anogenital Warts to Intralesional Treatment With Recombinant alpha-2 Interferon."
Trofatter, K. F., Jr., (1986). "Human Lymphoblastoid Interferon (Wellferon) in Primary Therapy of Two Children with Condylomata Acuminata." Obset. Gynecol. 67, 137-40.

(List continued on next page.)

Primary Examiner—Howard E. Schain
Attorney, Agent, or Firm—Dykema Gossett

[57] ABSTRACT

A pharmaceutical composition which includes human alpha-interferon, sodium dodecyl sulfate and a pharmaceutically acceptable vehicle is described. A method of using the pharmaceutical composition as a topical therapeutic agent in the treatment of condyloma acuminata is also provided.

8 Claims, No Drawings

OTHER PUBLICATIONS

Szoke, B. (1986). "Condyloma Acuminatum Treated With Human Leukocyte Interferon." J. Urology 135, 1247–48.

Vance, J. C. (1986). "Intralesional Recombinant Alpha-2 Interferon for the Treatment of Patients with Condyloma Acuminatum or Verruca Plantaris." Arch. Dermatol. 122, 272–77.

Geffen, J. R. et al. (1984). "Intralesional Administration of Large Doses of Human Leukocyte Interferon for the Treatment of Condylomata Acuminata. J. Infectious Diseases 150, 612–15.

Einhorn, N. et al. (1983). "Systemic Interferon Alpha Treatment of Human Condylomata Acuminata." Acta Obstet. Gynecol. Scand. 62, 285–87.

Gross, G. (1988). "Interferon and Genital Warts." JAMS 260, 2066 (letter to the editor; Oct. 14, 1988).

Gross, G. et al. (1986). "Alpha Interferon in Condylomata Acuminata and Juvenile Diabetes Mellitus." Dtsch. Med. Wochenschr. III (36) 1351–1355 (Sep. 5, 1986) (abstract only).

Albrecht, G. (1986). "Condylomata Acuminata, Recent Aspects of Clinical Signs, Pathogensis and Therapy." Z. Hautkr 61(7), 457–62 (Apr. 1986) (abstract only).

Douglas, J. M., Jr., (1986). "The Effect of Asymptomatic Infection with HTLV-III on the Response of Anogenital Warts to intralesional Treatment With Recombinant alpha-2 Interferon." J. Infec. Dis 154, 331–34.

Pazin, G. J. et al. (1982). "Effects of Interferon-Alpha on Human Warts." J. Interferon Res. 2, 235–43.

Gall, S. A. et al. (date unknown). "Interferon for the Treatment of Resistant Condyloma Acuminata." Soc. Gynecol. Oncol. p. 264 (abstract no. 29).

Gibson, J. R. et al. (date unknown). "Interferon for in the Treatment of Persistent Viral Warts." B.S.I.D. Annual Meeting, 694–95 (abstract only).

Scott, G. et al. (1979). "Effects of Injection of Small Doses of Human Fibroblast Interferon into Genital Warts." Br. J. Vener. Dis. 55, 442–445.

Gross, G. et al. (1986). "Alpha Interferon in Condyloma Acuminata and Juvenile Diabetes Mellitas." Dtsch. Med. Wochenschr. 3 (36), 1351–55.

Gross, G. (1988). "Interferon and Genital Warts." JAMA 260, 2066 (letter to editor).

Reichman, R. et al. (1985). "A Multicenter Study of Interferon Alpha-nl Wellferon) Treatment For Refractor Condyloma Acuminate." Proc. Intersci. Conf. Antimicrobial Agents Chemother. 106 (Abst. 96).

Gross, G. et al. (1984) "Bowenoid Dysplasia in Human Papillomavirus-16 DNA Positive Flat Condylomas During Interferon Treatment." Lancet 1467–68.

Ikic, D. et al. (1975). "Preliminary Study of the Effect of Human Leukocyte Interferon on Condyloma Acuminate in Women." Proc. Symp. Clinical Use of Interferon, Yugoslav Acad. Sci. & Arts, Zagreb, Yugoslavia, pp. 223–227. (Not available at present time.)

Ikic, D. et al. (1975). "Double Blind Clinical Study with Human Leukocyte Interferon in the Therapy of Condylomata Acuminata." Proc. Symp. Clinical Use of Interferon, Yugoslav Acad. Sci. & Arts, Zagreb, Yugoslavia, pp. 229–233 (not available at present time.)

Stewart, W. E. (1989). "Evaluation of Natural Alpha Interferon" GenoFeron Ointment For Therapy of Refractory and Recurrent Condyloma Acuminata. Open Trial (Unpublished data.)

Stewart, W. E. (1989). "Evaluation of Natural Alpha Interferon" GenoFeron Ointment For Therapy of Refractory and Recurrent Condyloma Acuminata: Double–blind, Placebo–controlled Trial. (Unpublished data.)

Einhorn, N. et al. (1983). Systemic Interferon Alpha Treatment of Human Condylomata Acuminata. Acta Obstet. Gynaecol. Scand. 62, 285–287.

Szoke, B. (1986). Condyloma Acuminata Treated with Human Leukocyte Interferon, J. Urol. 135, 1247–1248.

Gall, S. et al. (1986) Efficacy of Human Lymphoblastoid Interferon in the therapy of Resistant Condyloma Acuminata. Obstet. Gynecol. 67, 643–651.

Gall, S. et al. (1985). Interferon for the Therapy of Condyloma Acuminatum. Amer. J. Obstet. Gynecol. 153, 157–163.

Trofatter, K. et al. (1986). Human Lymphoblastoid Interferon (Wellferon) in Primary Therapy of two children with Condyloma Acuminata. Obstet-Gynecol. 67, 137–140.

Trofatter, K. et al. (1986). Combination of NSAIS and Wellferon: A Controlled clinical trial in Genital Warts. In: The Biology of the Interferon System-1985 (W. E. Stewart I) and H. Schellekens, Edit) Elsevier, Amsterdam, pp. 471–477.

Schonfeld, A. et al. (1984). Intramuscular Human Interferon-Beta Injections in Treatment of Condyloma Acuminata. Lancet 1, 1038–1042.

Geffin, J. et al. (1984). Intralesional Administration of Large Doses of Human Leukocyte Interferon for the Treatment of Condyloma Acuminata. J. Infect. Dis. 150, 612–615.

Friedman-Kien, et al. (1988). Natural Interferon Alfa for Treatment of Condyloma Acuminata. JAMA, 259, 533–538.

Eron, L. et al. (1986). Interferon Therapy for Condyloma Acuminata, N. Eng. J. Med. 315, 1059–1064.

Douglas, J. et al. (1986). The effect of infection with HTLV-III on the Response of Anogential Warts to Intralesional Treatment with Recombinant Alpha-2 Interferon. J. Infect. Dis. 154, 331–334.

Vance, J. et al. (1986). Intralesional Recombinant Alpha-2 Interferon for the treatment of patients with Condyloma Acuminata or Verruca Plantaris. Arch. Dermatol. 122, 273–277.

Marcovici, R. et al. (1983). Human Fibroblast Interferon Therapy in Patients with Condyloma Acuminata. ISR. J. Med. Sci. 19, 104.

Vesterinen, E. et al. (1984). Treatment of Vaginal Flat Condyloma with Interferon Cream. Lancet 1, 157.

Vesterinen, E. et al. (1984). Topical Treatment of Flat Vaginal Condyloma with Human Leukocyte Interferon. Obstet. Gynecol. 64, 535,538.

Keay, S. et al. (1988). Topical Interferon for Treating Condyloma Acuminata in Women, J. Infect. Dis. 158, 934–939.

Brzoska, J. et al. (1989). Phase II Clinical Trials of Interferon Beta Gel (Fibroblast-gel) in Dermatological Diseases, J. Interferon Res. 9, (Suppl.2) S. 257.

Unknown excerpt "Mean Values for Key Clinical Laboratory Parameters at Weeks Two and Six."
Gross & Albrect Abstracts on Condylomata Acuminatum.
NIH vol. 260, No. 19 (1988).
Gall, S. et al. "Systemic Alpha-Interferon for Condyloma Acuminata," Obstetrics and Dynecology, vol. 67, No. 5, May 1986.
Gall & Silva Abstracts on Condyloma Acuminatum & Interferon.
Gross & Eron abstracts on Condyloma Acuminatum & Interferon.
Vance, Strander and Douglas Abstracts on Condyloma Acuminatum & Interferon.
Abstracts, Society of Gynecological Oncologists–#29 Gall, et al. Interferon for the Treatment of Resistant Condyloma Acuminata.
Gibson, J. R., Harvey, S. G. "Interferon in the Treatment of Persistent Viral Warts," BSID Annual Meeting.
Pazin, G. J., et al. Effects of Interferon-Alpha on Human Warts, Journal of Interferon Research, vol. 2, No. 2, 1982.
(Internal Report, Nat'l Geno Science) Roberts, W. S. Double Blind, Pace 60-Controlled, Crossover Trial of Human Interferon-Alpha.
(Internal Report, Nat'l Geno Sciences) "Clinical Documentation"
(Internal Report, Nat'l Geno Science) Ramesh, T. "Expert Report on the Clinical Documentation."

Reichman, R. et al. (1985) A multicenter Study of Interferon Alfa-nl (Wellferon) Treatment for Refractory Condyloma Acuminata. Proc. Intersci. Conf. Antimicrobial Agents Chemother. 106, Abst. 96.
Gross, G. et al. (1986). Alpha Interferon in Condyloma Acuminata and Juvenile Diabetes Mellitus. Dtsch. Med. Wochenschr. 3 (36), 1351–1355.
Gross, G. (1988). Intereron and genital warts. JAMA, 260, 2066.
Gross, G. et al. (1985). Bowenoid Dysplasia in Human Papillomavirus-16 DNA Positive Flat Condylomas during Interferon Treatment. Lancet 1, 1467–1468.
Scott, G. and Csonka, G. (1979). Effects of Injection of Small doses of Human Fibroblast Interferon into Genital Warts. Br. J. Vener. Dis. SS, 442–445.
Ikic, D. et al. (1975). Double Blind Clinical Study of Condyloma Acuminata in the Therapy with Human Leukocyte Interferon. Proc. Symp. Clinical Use of Interferon. Yugoslav Acad. Sci. Arts., Zagreb, Yugoslavia, pp. 229–238.
"Protection against herpes simplex virus infection in mice by recombinant murine interferon-B in combinatio with antibody.
Yuji Kumano, Masahiro Yamamoto and Ryoichi Mori, Feb. 28, 1987, pp. 289–299, pp. 1–6 of Abstract of Condylomata Acuminata.
Letter to Editor "Interferon and Genital Warts" JAMA. Oct. 14, 1988, vol. 260, No. 14.

METHOD FOR TREATING CONDYLOMA ACUMINATUM WITH INTERFERON

This is a continuation of copending application Ser. No. 07/299,707 filed on Jan. 23, 1989, now abandoned.

BACKGROUND OF THE INVENTION

Condyloma acuminata, commonly referred to as genital warts, are known to be benign, fibro-epithelial tumors associated with various papilloma viruses. Condyloma acuminata is a sexually-transmitted disease, the occurrence of which is increasing rapidly. Genital warts are frequently found on or near the vulva, in the vagina, and about the rectum or penis. The manifestation of genital warts begins as an itching sensation whereupon a small papule develops. Depending upon the extent of the lesion, continued itching and a discharge may occur.

A number of prior art treatments are known, including the use of cryotherapy and the surgical excision of the warts. Traditional treatment modalities also include the use of podophyllin which is applied topically to the lesions. Podophyllin treatment is typically repeated at intervals of seven to fourteen days and may cause irritation of the affected area.

It is known that interferons exert a broad spectrum of biological activity such as anti-viral, anti-proliferative and immunomodulatory activities. Following the characterization of interferon by Isaacs and Lindeman, interferon has been the subject of intense research to determine its molecular structure and genetic basis as well as to develop processes for its synthesis and protocols for clinical applications. The exact mechanisms by which its anti-tumor, anti-viral and immune system activities occur are not fully understood. A number of references are available which detail the history and scope of interferon research such as DeMaeyer et al., "Interferons" appearing as Chapter 5 in *Comparative Virology*, Vol. 15, pp. 205-284, Plenum Press, N.Y., N.Y. (1979); Cantrell, "Why Is Interferon Not In Clinical Use Today" appearing in *Interferon* 1979, I. Gresser, ed., Vol. 1, pp. 1-28, Academic Press, London (1979); Stewart, "The Interferon System" Springer-Verlag, N.Y., N.Y. (1979); Dunnick, et al., "Clinical Trials with Exogenous Interferon," *J. Infect. Diseases*, 139, No. 1, pp. 109-123 (1979); and *Proc. Rov. Soc. London* (Ser. B), Vol. 147, pp. 256 et seq. (1957) and U.S. Pat. No. 3,699,222.

The nomenclature which has been adopted to classify interferons is generally standardized. To qualify as an interferon, a factor must be a protein which exerts non-specific, anti-viral activity at least in homologous cells through cellular metabolic processes involving synthesis of both RNA and protein. Interferon is abbreviated "IFN," and each interferon is identified according to the animal of origin. Thus, human interferon is designated "Hu IFN." Interferons are classified into types on the basis of antigenic specificities. Type designations for the most common interferons are alpha, beta and gamma which correspond to previous designations of leukocyte, fibroblast, and Type II (immune) interferons, respectively. Alpha and beta interferons are typically acid-stable with gamma interferons being acid labile. Interferons may be produced through genetic engineering and are generally referred to as "recombinant interferons." Recombinant interferons are designated in accordance with the foregoing nomenclature, for example, "Hu rIFN-$\alpha$" for human recombinant alpha interferon. For the purposes of the present invention, all references to alpha interferon will be to natural or non-recombinant human alpha interferon unless otherwise specified.

Human alpha interferon is known to be effective in the treatment of several viral infections, including chronic hepatitis B virus infections and herpes zoster infections ("Effect of Human Leukocyte Interferon on Hepatitis B Virus Infection in Patients with Chronic Active Hepatitis," *N. Engl. J. Med.*, Vol. 295; "Human Leukocyte Interferon for the Treatment of Herpes Zoster in Patients with Cancer," *N. Engl. J. Med.*, Vol. 298). More recently, human alpha interferon has been found to suppress the in vitro replication of AIDS virus ("Human Alpha- and Beta-Interferon but not Gamma Suppress the In Vitro Replication of LAV-HTLV-III and ARV-II," *J. Interferon Res* 6:143; "Direct and Cell-Mediated Effects of Interferon Alpha and Gamma on Cells Chronically Infected with HTLV-III," *J. Interferon Res* 6:543). Also, numerous techniques have been developed to purify interferon, for example the method described in U.S. Pat. No. 3,144,390 to Burke.

In addition, others have treated condyloma acuminata with recombinant human alpha-interferon by the subcutaneous and intramuscular injection of interferon. Both recombinant human alpha-interferon and human beta-interferon have been used in this manner. (See, G. Gross, et al., "Alpha-Interferon in Condylomata Acuminata and Juvenile Diabetes Mellitus," *Dtsch-Med.-Wochenschr*, 1986, Sep. 5, III(36), pp. 1351-5; A. Schonfeld, et al., "Intramuscular Human Interferon Beta Injections in Treatment of Condylomata Acuminata," *Lancet*, 1984, May 12, I(8385), pp. 1038-42). Treatment of condylomata acuminata with interferon typically involves injection directly into the warts. Associated side effects may include fever, chills, myalgia, headache, fatigue and leukopenia.

There are also known topical uses of interferon, for example, as a prophylactic which is effective against the transmission of rhinovirus infections between infected subjects and uninfected subjects. As described in "Prophylactic Efficacy of Intranasal Alpha-Interferon Against Rhinovirus Infections in the Family Setting," *N. Engl. J. Med.*, Vol. 314, No. 2, the preparation and use of alpha-interferon along with a pharmaceutically acceptable excipient in the form of an intranasal spray is described. The alpha-interferon spray was administered as a metered aerosol. Topical application of alpha-interferon has also been used for the treatment of dendritic herpes keratitis.

Also, in U.S. Pat. No. 4,017,600, one of the inventors of the present invention describes a method for reactivating interferon using a combination of an agent for disrupting non-covalent bonds, an agent for reducing disulfide bridges, and an anionic or cationic surface-active agent. In U.S. Pat. No. 3,981,991, one of the inventors of the present invention describes a method for stabilizing interferon by treatment in the manner described in U.S. Pat. No. 4,017,600, and the use of sodium dodecyl sulfate is specifically disclosed.

The present invention provides a composition and a method for using this composition in the treatment of condyloma acuminata.

SUMMARY OF THE INVENTION

In accordance with the present invention there is provided in one embodiment a therapeutic composition which includes human alpha-interferon and a surfactant, preferably sodium dodecyl sulfate. The human alpha-interferon in one embodiment is natural human alpha-interferon. The human alpha-interferon and surfactant are combined with a pharmaceutically acceptable carrier or vehicle to form an ointment or the like for topical administration directly to condyloma acuminatum lesions of a human patient. Thus, the present invention also provides a method for treating condylomata acuminata with a therapeutically effective amount of a composition which includes human alpha-interferon and sodium dodecyl sulfate in a suitable vehicle by topical administration of the composition directly to the lesions. The method of the present invention is efficacious in clearing condyloma acuminata lesions and in preventing recurrence of the lesion.

Further aspects and advantages of the present invention will become apparent upon consideration of the following detailed description including the illustrative examples.

DETAILED DESCRIPTION OF THE PREFERRED EMBODIMENTS

In the first step of the present invention, a purified source of human alpha-interferon is provided. As will be appreciated by those skilled in the art, and as previously indicated, interferon is a low-molecular weight polypeptide produced as an excretion from various types of mammalian cells. Its properties, chemical nature and methods of preparation have been extensively studied and documented. In the present invention, human alpha-interferon produced by human leukocyte cells or in transformed leukocyte cells known as lymphoblastoid lines are preferred. Human alpha-interferon has been purified to homogeneity (M. Rubenstein, "Human Leukocyte Interferon: Production, Purification to Homogeneity and Initial Characterization," *PNAS*, 76:640-44 (1979)).

Suitable human alpha-interferon for use in the present invention has an average molecular mass of from about 10,000 to 30,000 daltons and preferably from about 13,000 to 25,000 daltons. Recombinant human alpha-interferon may also be suitable. The precise amino acid sequence of the human alpha-interferon used in the present invention is not deemed to be critical. It is noted that a number of alpha-interferon species are known, usually designated by a numeral after the Greek letter. Human alpha-interferon suitable for use in the present invention can be obtained from a number of commercial suppliers. For clinical trial purposes, a suitable human alpha-interferon for use in the present invention is produced by National Geno Sciences, Inc. Since the methods of preparing and purifying human alpha-interferon are well known, the complete protocol will not be set forth herein.

The specific activity of the human alpha-interferon used in the present invention is between about $1 \times 10^5$ international units per milligram of protein and about $1 \times 10^8$ international units per milligram of protein, preferably between about $1.0 \times 10^6$ international units per milligram of protein and about $9.0 \times 10^6$ international units per milligram of protein, and most preferably about $1.55 \times 10^6$ international units per milligram of protein. The protein content of the alpha-interferon can be determined in a number of manners, including by the Lowry method for protein determination with bovine serum albumin as the reference. Specific activity may be determined by measuring the anti-viral activity as compared to the NIH reference standard. In the final therapeutic composition of the present invention, which preferably comprises an ointment, gel or lotion, and which contains both human alpha-interferon and sodium dodecyl sulfate, as will be more fully described, one gram of the therapeutic gel includes from about 0.01 milligram to about 1 milligram of human alpha-interferon and most preferably about 0.1 milligram of human alpha-interferon. In other words, alpha-interferon comprises from about 0.001% to about 0.1% by weight of the final composition and most preferably about 0.01% by weight. It is generally preferred that each gram of the final gel composition contain from about $1 \times 10^4$ to about $1 \times 10^8$ and most preferably about $1 \times 10^5$ I.U. human alpha-interferon per gram of gel or ointment.

In addition to human alpha-interferon, the surprising results of the present invention are obtained in one embodiment by combining human alpha-interferon with a surfactant, preferably sodium dodecyl sulfate, although it is believed that some therapeutic results may be attained without surfactant. While tests have indicated that the use of sodium dodecyl sulfate in connection with the present invention provides excellent therapeutic results, it is contemplated that other surfactants may also be useful in the present invention such as sodium octyl sulfate, sodium decyl sulfate, sodium tetradecyl sulfate, sodium hexadecyl sulfate, sodium octadecyl sulfate or combinations of these surfactants. A surfactant is present in the therapeutic gel or ointment of the present invention in the range of from about 0.01 milligram of sodium dodecyl sulfate to about 0.20 milligram, more preferably from about 0.1 milligram to about 0.17 milligram and most preferably about 0.15 milligram per gram of gel or ointment. In other words, the surfactant comprises from about 0.001% to about 0.02% by weight of the final composition, preferably from about 0.01% to about 0.017% and most preferably about 0.015% by weight of the final composition.

A number of acceptable carriers or vehicles are suitable for use in the present invention which is preferably administered as a gel, ointment, or lotion. Other viscous liquid carriers may also be suitable. These inert carriers, that is, inert with respect to the active ingredients, human alpha-interferon and surfactant, are selected with respect to the solubility of the interferon component and the desired physical characteristics of the final composition. Of course, the carriers must be non-allergenic. Parafin-based ointments and oil and water emulsion creams are suitable for use herein. Lanolin and petroleum-based carriers are also suitable. Aqueous gels, such as those formed with hydroxymethylcellulose are also preferred for use herein. Heat-sterilizable aqueous gels compising a pharmaceutically acceptable glycol and a cellulose derivative which is heat-sterilizable are particularly preferred. One suitable preferred glycol is propylene glycol. A method of preparing a suitable pharmaceutical gel composition for use as a carrier in the present invention is described in U.S. Pat. No. 4,604,384, the disclosure of which is incorporated herein by reference.

Viscous aqueous solutions which are thickened by addition of selected gums or cellulose-derived viscosity building agents in the nature of lotions or creams are also preferred as the vehicle or carrier for the interferon and sodium dodecyl sulfate used in the present invention. Generally, the viscosity of the pharmaceutical composition used in the present invention will range from about 25 cps to the viscosity of a still gel. Of course, any such vehicle must substantially uniformly suspend or dissolve the active ingredients. Other vehicles which may be useful in the present invention are described in U.S. Pat. No. 4,188,373, the disclosure of which is incorporated herein by reference. The most preferred carrier for use herein includes both lanolin and petrolatum.

The protocol for preparing a therapeutic interferon-based ointment for use in the present invention may vary somewhat so long as the principles of the present invention are faithfully observed. In one suitable protocol, human alpha-interferon is dialyzed against ammonium bicarbonate at neutral pH and is then lyophilized. The lyophilized interferon containing powder is then pulverized in sodium dodecyl sulfate, and the emulsified sample is added to a small volume of sterile mineral oil. This intermediate composition is then added to a volume of solution containing anhydrous lanolin and petrolatum which is then stirred for about an hour at 37 degrees C. The therapeutic ointment can then be stored in sterile vials. As stated, a final alpha-interferon concentration of about $1 \times 10^5$ IU per gram of ointment is particularly preferred.

In the next step of the present invention, an initial topical application of the therapeutic ointment of the present invention is carried out in the following manner. The therapeutic composition of the present invention, for example in the form of an ointment, is applied to the condyloma acuminatum lesions and the immediately surrounding areas, preferably three times daily, with approximately a six to ten-hour delay between applications. Thus, in one embodiment, the present invention comprises administering an effective amount of the pharmaceutical composition of the present invention which includes human alpha-interferon and a surfactant, preferably sodium dodecyl sulfate, to condyloma acuminata lesions on a human patient. As stated, these lesions may appear in a number of areas, and application is contemplated in genital areas such as the vulva, vaginal areas, and about the penis, as well as anal areas. Application of the pharmaceutical composition of the present invention may be carried out as often as five times daily and preferably approximately 1 gram of the composition per day per patient is utilized. Of course, this may vary depending upon the extent of the affected area. Daily application is continued for a period up to approximately three months, and in many instances, significant remission and complete clearance of the lesions occurs within three to four weeks.

Although in the preferred embodiment the present invention includes the use of a surfactant, it is intended that in the broadest sense, the method of treating condyloma acuminatum provided by the present invention includes the use of a therapeutic composition containing only human alpha-interferon in a suitable vehicle such as an ointment which is applied topically directly to the affected area. It is believed that the addition of a surfactant provides synergistic effect and promotes stabilization and absorption of the interferon at the affected site.

The following examples further illustrate the invention and are not intended to limit the scope of the invention in any way.

EXAMPLES

Human alpha-interferon in phosphate-buffered sodium chloride 0.8% supplied by National Geno Sciences, Inc. at a concentration of $3 \times 10^6$ IU interferon per ml (containing from 1 to 3 milligrams protein per ml), was dialized against 0.83% ammonium bicarbonate pH 7.0 for twenty-four hours at 4 degrees C. and was then lyophilized. The lyophilized interferon-containing powder was then pulverized in 0.1 gram of electrophoretic-grade sodium dodecyl sulfate per $10^7$ units, and the emulsified sample was then added to a small volume of sterile mineral oil to a final concentration of approximately $1 \times 10^7$ IU per ml. This was then added to a volume of solution containing anhydrous lanolin and petrolatum (at 1:100 gram ratios) with stirring for one hour at 37 degrees C. to obtain a final concentration of $1 \times 10^5$ IU of interferon per gram of ointment.

The ointment was then dispensed into sterile 20-gram ointment vials and stored at 4 degrees C.

EXAMPLE 1

A patient afflicted with condyloma acuminatum in the genital area with a lesion approximately 10 millimeters in diameter was treated by a topical application of the above-described alpha-interferon/SDS-based composition of the present invention with instructions to apply the composition three times daily. In approximately two weeks, there was a ten percent decrease in the size of the lesion.

EXAMPLE 2

A patient afflicted with condyloma acuminata with multiple lesions in the genital area, a typical lesion being approximately 15 millimeters in diameter, was treated in accordance with the present invention. After approximately two months treatment, there was approximately a 50 percent remission in the lesions.

EXAMPLE 3

In this example, the patient was afflicted with condyloma acuminatum with a lesion of approximately 25 millimeters in the rectal area and a lesion of approximately 6 millimeters in the penile area. After approximately six weeks, there was slight improvement in the rectal lesion and marked improvement in the penile lesion.

EXAMPLE 4

A patient afflicted with condyloma acuminatum with a lesion in the rectal area of approximately 20 millimeters was treated in accordance with the present invention. After eight weeks, there was a 90 percent clearance, and after thirteen weeks of treatment, there was 100 percent clearance of the lesion. In a follow-up examination eighteen months after treatment, there was no recurrence of the lesion.

EXAMPLE 5

A patient afflicted with a condyloma acuminatum lesion of approximately 21 millimeters was treated in accordance with the present invention for approximately twelve weeks, after which the affected area was 95 percent cleared.

EXAMPLE 6

A patient afflicted with a condyloma acuminatum lesion of approximately 30 millimeters and was treated in accordance with the present invention. After approximately twelve weeks treatment, the lesion was 95 percent reduced in size.

EXAMPLE 7

A patient afflicted with a condyloma acuminatum lesion of approximately 12 millimeters in the genital region and a lesion of approximately 5 millimeters in the area of the patient's lips was treated in accordance with the present invention. There was a slight improvement in the genital lesion, but no improvement in the lesion in the oral area.

While a particular embodiment of this invention is shown and described herein, it will be understood, of course, that the invention is not to be limited thereto since many modifications may be made, particularly by those skilled in this art, in light of this disclosure. It is contemplated therefore by the appended claims to cover any such modifications as fall within the true spirit and scope of this invention.

What is claimed is:

1. A method for the treatment of condyloma acuminatum which comprises administering an effective amount of a pharmaceutical composition consisting essentially of human alpha-interferon and a sodium dodecylsulfate in a pharmaceutically acceptable carrier topically directly to condyloma acuminatum lesions.

2. The method recited in claim 1, wherein said human alpha-interferon is naturally occurring human alpha-interferon.

3. The method recited in claim 1, wherein said human alpha-interferon is recombinant human alpha-interferon.

4. The method recited in claim 1, wherein said carrier is selected from the group consisting of ointments, creams, gels, and lotions.

5. The method recited in claim 1, wherein said human alpha-interferon is present in said composition in an amount from about 0.01 to about 1.0 milligram of alpha-interferon per gram of said pharmaceutical composition.

6. The method recited in claim 1, wherein said surfactant is present in said pharmaceutical composition in an amount from about 0.01 and about 0.2 milligram sodium dodecylsulfate per gram of said pharmaceutical composition.

7. The method recited in claim 1, wherein each gram of said pharmaceutical composition contains from about $1 \times 10^4$ to about $1 \times 10^8$ IU of human alpha-interferon.

8. A method for the treatment of condyloma acuminatum which comprises the periodic topical application of a pharmaceutical composition consisting of about 0.01% by weight recombinant human alpha-interferon, said recombinant human alpha-interferon having a specific activity of about $1.55 \times 10^6$ International Units, about 0.015% sodium dodecyl sulfate and a pharmaceutically acceptable carrier, said recombinant human alpha-interferon and said sodium dodecyl sulfate being in admixture with said pharmaceutically acceptable carrier.

* * * * *